(12) United States Patent
Hoeprich et al.

(10) Patent No.: US 11,844,675 B1
(45) Date of Patent: Dec. 19, 2023

(54) SURGICAL SPONGE

(71) Applicants: David Hoeprich, Rocky River, OH (US); Mark Hoeprich, Springboro, OH (US)

(72) Inventors: David Hoeprich, Rocky River, OH (US); Mark Hoeprich, Springboro, OH (US)

(73) Assignee: Torbern Company, LTD, Cincinnati, OH (US)

( * ) Notice: Subject to any disclaimer, the term of this patent is extended or adjusted under 35 U.S.C. 154(b) by 783 days.

(21) Appl. No.: 16/530,610

(22) Filed: Aug. 2, 2019

Related U.S. Application Data

(60) Provisional application No. 62/713,688, filed on Aug. 2, 2018.

(51) Int. Cl.
| | | |
|---|---|---|
| *A61F 13/44* | (2006.01) | |
| *A61B 90/98* | (2016.01) | |
| *A61B 90/00* | (2016.01) | |
| *A61F 13/36* | (2006.01) | |

(52) U.S. Cl.
CPC .............. *A61F 13/44* (2013.01); *A61B 90/98* (2016.02); *A61B 2090/0804* (2016.02); *A61F 13/36* (2013.01)

(58) Field of Classification Search
CPC .......... A61F 13/44; A61F 13/36; A61B 90/98; A61B 2090/0804
See application file for complete search history.

(56) References Cited

U.S. PATENT DOCUMENTS

| | | | | |
|---|---|---|---|---|
| 3,911,922 | A | * | 10/1975 | Kliger .................... A61F 13/44 604/362 |
| 4,477,256 | A | * | 10/1984 | Hirsch .................. A61F 13/206 604/362 |
| 4,718,897 | A | * | 1/1988 | Elves ....................... D04H 5/08 604/362 |
| 7,465,847 | B2 | * | 12/2008 | Fabian .................... A61F 13/44 604/362 |
| 2005/0016776 | A1 | | 1/2005 | Ballard |
| 2007/0219516 | A1 | * | 9/2007 | Patel ....................... A61F 13/44 604/362 |
| 2014/0194733 | A1 | * | 7/2014 | Goforth .................. B82Y 30/00 29/428 |

OTHER PUBLICATIONS

Serebrennik ("What is the difference between woven and nonwoven gauze?", Sep. 20, 2016) (Year: 2016).*

* cited by examiner

*Primary Examiner* — Seung H Lee

(57) ABSTRACT

An improved surgical sponge having a contrast agent, such as bismuth beads, secured to the sponge material in a unique pattern of a type not found in nature or in human anatomy. The unique pattern is preferably spaced dots or circles having various sizes and spacing, potentially arranged in a matrix of rows and columns. The desired unique pattern is arranged such that the dots or other non-natural shapes are large enough to remain visible, while small enough to avoid adversely affecting the pliability and absorption of the sponge.

15 Claims, 4 Drawing Sheets a.) homogenous mixture of bismuth and adhesive arranged in non-anatomic geometric pattern
b.) surgical sponge comprised of cotton-like absorbent material

SURGICAL SPONGE

CROSS REFERENCE TO RELATED APPLICATIONS

The present application claims priority from U.S. Patent Application Ser. No. 62/713,688, filed Aug. 2, 2018, the entire subject matter of which is incorporated herein by reference.

TECHNICAL FIELD

The present application relates to a surgical sponge, and more specifically, to an improved surgical sponge having a unique surface pattern of bismuth applied and surface adhered to enable x-ray identification.

BACKGROUND OF THE INVENTION

Surgical sponges or surgical gauze is used during surgical procedures, for example, for absorbing blood and tissue fluids, and protecting biological structures during surgical procedures. Unfortunately, although many strategies are used and many precautions are taken, some surgical sponges may not be removed prior to closing a surgical wound following a surgery. Such missed sponges result in the potentially serious surgical complication of retained surgical foreign bodies for patients, or gossypiboma. In fact, retained foreign bodies consistently top The Joint Commission's sentinel event list. The Joint Commission is the oldest and largest standards-setting and accrediting body for health care in the United States.

Surgical or gauze sponges for medical use are normally provided in many sizes, plies, and fabrics. Available gauze sponges include both woven cotton fabrics which have a more coarse texture, and non-woven fabrics of a poly-rayon blend material, or a polymer material, which leave less lint residue during use. One technology commonly used for detecting surgical sponges within a patient having surgery, is to provide gauze sponges with a radiopaque strip or thread so that they can be readily detected by X-ray imaging and removed before being accidentally left inside a patient's body. Typically, such surgical sponges utilize a thread containing barium (Ba) or barium sulfate (BaSO4) to generate contrast and aid in the visual detection of a retained surgical sponge location while using an x-ray imaging device. The barium impregnated thread is generally sewn in, or otherwise attached to, the surgical sponge material.

Other alternative technologies or sponge tracking systems for counting and removing surgical sponges include radio-frequency identification (RFID) sponges and associated reader systems. Such systems use sponges embedded with a radio-frequency chip, so each surgical sponge is individually provided with an RFID chip, and the reader system is provided to detect and count each RFID chipped sponge. Despite the use of such expensive RFID marked sponges and reader systems, and the use of such barium threads, or X-ray detectable sponges together with X-ray imaging procedures for reviewing the surgical site for missing sponges, surgical sponges are still accidently missed.

With respect to radiopaque sponges, it has been determined that the use of impregnated threads in a surgical sponge can mimic other types of biological structures during an X-ray imaging procedure, such as anatomic lines and organ shadows. Such lines and shadows limit the ability of medical teams to clearly determine whether a surgical sponge is being detected. As the number of retained surgical foreign bodies is a continuing problem for patient care, there is a need for an improved sponge that addresses this serious issue.

SUMMARY OF THE INVENTION

According to the improved surgical sponge of the present application, a new approach is provided to overcome prior difficulties with identification of surgical sponges using an X-ray imaging procedure.

The improved surgical sponge of this application utilizes a bismuth (Bi) marker material as the contrast agent in X-ray imaging. Bi has a high atomic number that lends itself to radiation attenuation, and thus, superior imaging contrast. Importantly, Bi radiation attenuation is superior to that of the conventionally used sponges with barium or barium sulfate compound impregnated threads. Bismuth also has uniquely low human toxicity for any of the heavy metal elements. Elemental bismuth is classified as "non-toxic," the least toxic heavy metal to humans. Bismuth in the form of various compounds has had very rare cases of documented toxicity. As a result, it is believed the improved bismuth treated surgical sponge will meet FDA approved specifications for approval for human use. Bismuth also has additional anti-bacterial properties that may provide advantages to patients. As a result, the use of bismuth as a contrast agent on a surgical sponge provides improved X-ray identification of retained foreign surgical bodies.

The improved surgical sponge having a bismuth marker or contrast agent, such as bismuth beads, may be applied to surgical sponges of various sizes and materials. The sponge materials may be either woven or non-woven fabrics, with the bismuth applied across a wider area of the sponge to provide a larger surface area of the contrast agent for improved detection. In experiments, the use of bismuth beads applied to a surgical sponge has been found to have very few disadvantages.

The manner in which the bismuth is applied to the surgical sponge will have little, if any, deleterious effects on the sponge pliability. A pliable adhesive may be used to secure the bismuth to one side of the sponge in order to function as a contrast fiducial, and will maintain flexibility in the contrast fiducial material so that there are no sharp or jagged edges to do damage in the surgical wound.

The manner in which the bismuth is applied to the surgical sponge also will have little, if any, deleterious effects on the sponge absorption abilities. The manner in which the bismuth is applied to the surgical sponge will generate improved contrast due to the use of a unique pattern as compared to the pattern generated by anatomic lines and organ shadows of the body. The unique pattern of the bismuth material applied to the surgical sponge is of a type not found in nature or in human anatomy, regardless of sponge orientation and how the sponge may be folded or manipulated. For example, dots or circle patterns of various sizes and spacing are unique patterns, easily applied and not found in human or animal anatomy or non-anatomic.

By applying the bismuth, and other high contrast fiducials, in the manner and size described, conventional X-ray imaging will be allowed to be operated at maximum x-ray techniques thereby washing out anatomic lines and organ shadows to allow any healthcare worker quick and definitive identification of the presence or absence of a surgical sponge bearing the unique pattern. This eliminates the need and delay for radiologist confirmation of the x-ray review of the surgical site, thereby saving time in the operating room and for the patient under anesthesia.

DETAILED DESCRIPTION OF THE DRAWINGS

Figure 1:
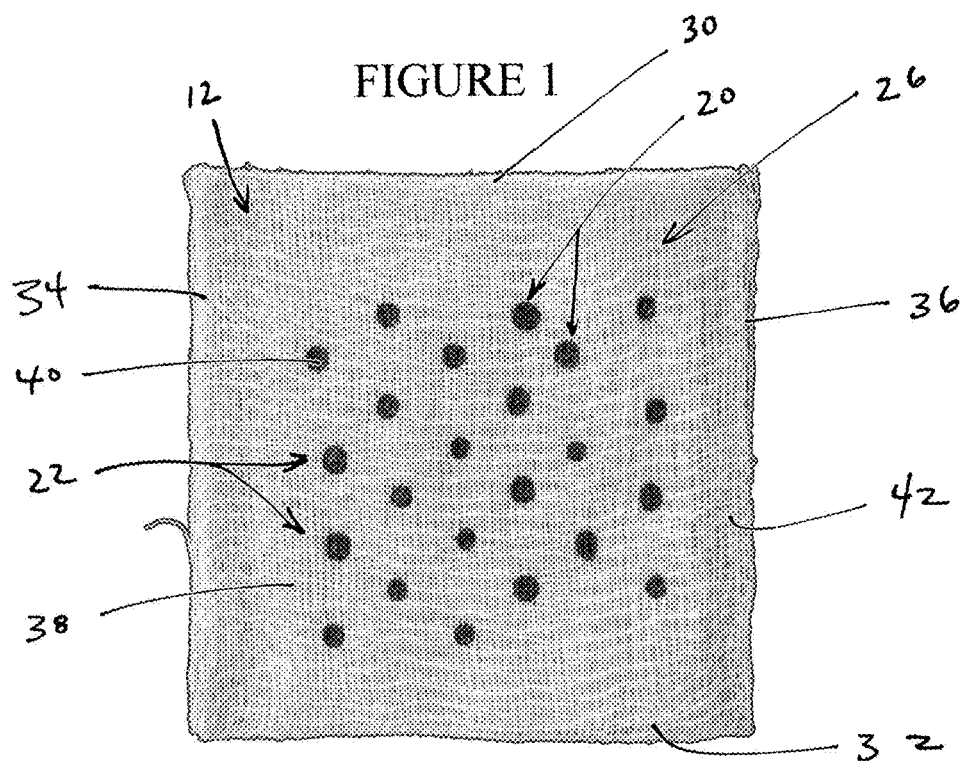
FIGS. 1 to 3 illustrate the improved surgical gauze or sponges of this application having bismuth contrast agent secured to the gauze material in various patterns of dots or circular shapes using various sizes and spacing.
Figure 2:
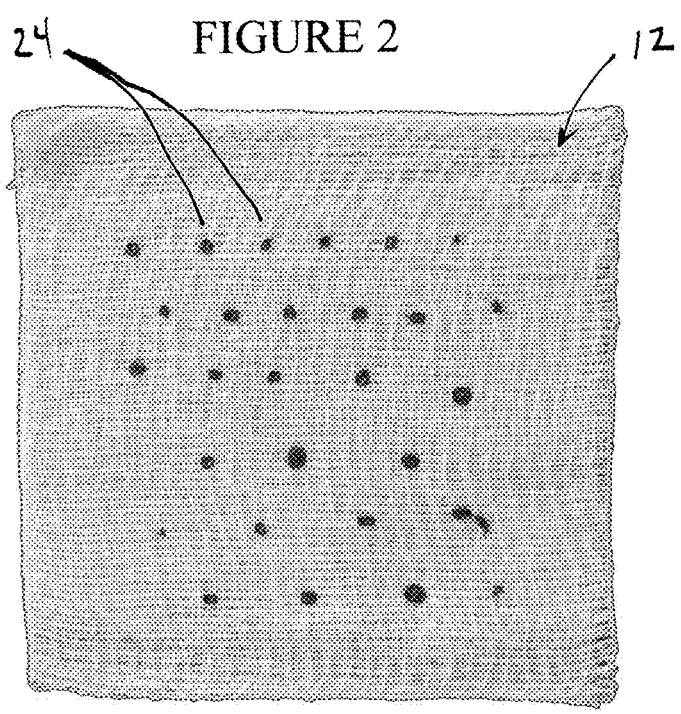
Figure 3:
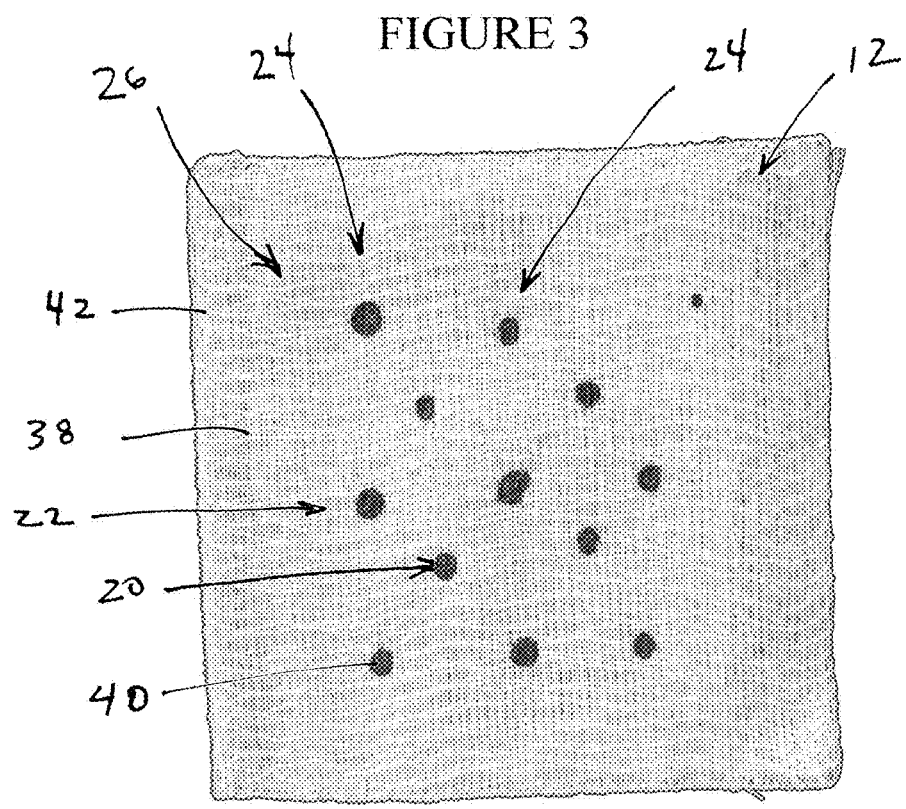

An improved surgical sponge 12 having a contrast agent 44, such as bismuth in the form of bismuth beads, secured to one surface 38 of a gauze sponge material 42 in a unique pattern of a type not found in nature or in human anatomy 26 is shown in FIGS. 1 to 3. The unique patterns 26 illustrated are spaced dots and/or circles 20 having various sizes and spacing. The desired unique pattern 26 is arranged such that the dots or shapes 20 are large enough to remain visible, while small enough to avoid adversely affecting the pliability and absorption features of the sponge 12. It should be understood that the illustrated pattern 26 of dots and/or circles 20 is only a sample of many non-natural, non-anatomic or non-naturally occurring shapes that could be adopted, such as pointed star shapes or triangles. As illustrated, the non-naturally occurring shapes may be arranged randomly, or in rows 22 and columns 24, such as the matrix pattern 26 spaced from the top and bottom edges 30, 32 of the sponge, across the surface area of the sponge and spaced from the left and right edges 34, 36 of the sponge. Bismuth beads 44 are commercially available, for example, from MilliporeSigma (formerly known as Sigma-Aldrich, www.sigmaaldrich.com), in sizes ranging from 1-5 mm.

Figure 7:
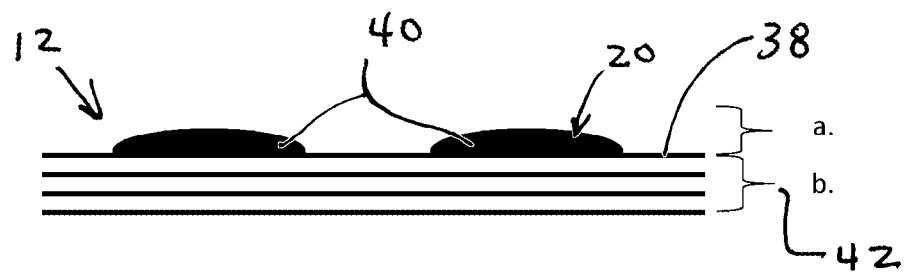
FIG. 7 illustrates a schematic cutaway side view showing the layers of the improved surgical sponge, where the adhesive and contrast agent are adhered to one surface of the sponge material, and the sponge material illustrated is a multi-ply woven gauze material. It is noted that the layers of the sponge are schematically shown spaced apart for ease of reference, but in practice, each layer is in direct contact with any neighboring layer, thereby forming a single composite material, as shown in FIGS. 1-3.

The adhesive used to adhere the contrast agent to one surface 38 of the sponge material 42 may be any appropriate commercially available adhesive. Silicone based adhesives are preferred, since once they are cured, they maintain flexibility, and pose less risk of forming edges that could cause tissue damage during surgery. The adhesive and contrast agent may be prepared using a wide variety of well known techniques, and applied on the sponge by a variety of common application techniques, such as by dusting, spraying or brushing, depending on the preparation of the adhesive and contrast agent. For example, the contrast agent and adhesive may be combined as a homogenous mixture 40 and then applied to the gauze sponge material 42 in the desired pattern 26 by dropping or brushing the mixture onto the gauze sponge material. As shown schematically in FIG. 7, the homogenous mixture of adhesive and contrast agent 40 is provided directly on the surface 38 of the gauze sponge material 42 in a layer of approximately 1 to 2 mm, and preferably a 1.5 to 2 mm thickness layer, in the shapes 20 and the desired pattern 26. Alternatively, the adhesive may be first applied in the desired pattern 26 to the gauze sponge material 42, after which the contrast agent is applied to the adhesive prior to curing. Where the adhesive is first applied in the desired shapes 20 and the unique pattern 26, followed by the contrast agent 44, it is understood that the contrast agent adheres only to the areas of applied adhesive. Contrast agent which does not contact and adhere to the adhesive material on the sponge material may be readily removed for reuse.

Figure 4:
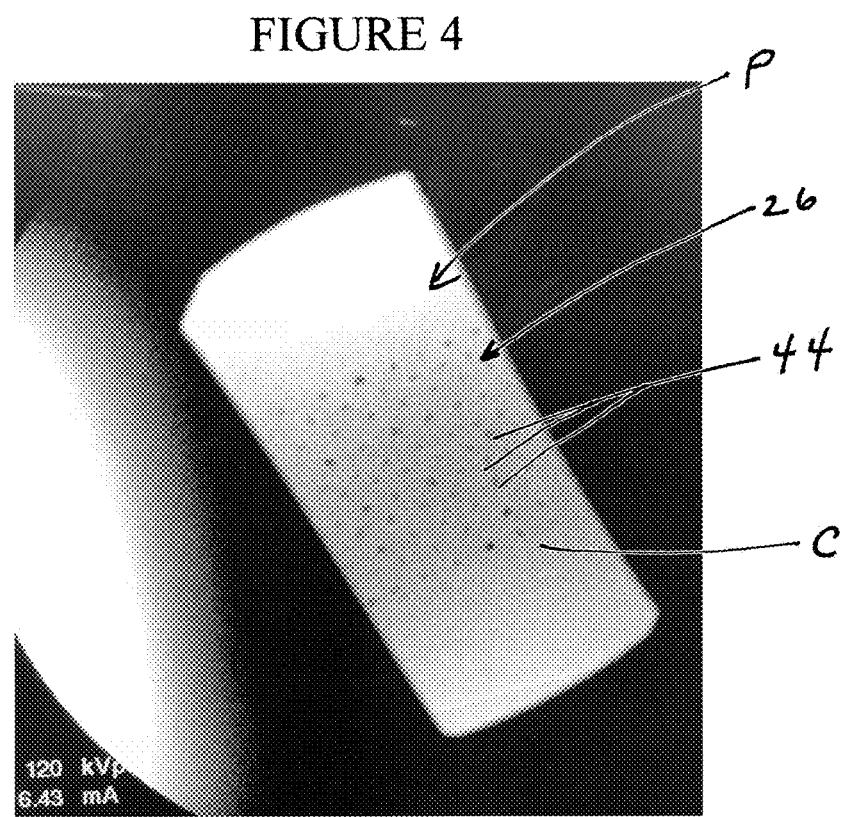
FIGS. 4 to 6 illustrate X-ray images taken of the surgical sponges of FIGS. 1 to 3 having the bismuth contrast agent, as filmed through an X-ray phantom specimen.
Figure 5:
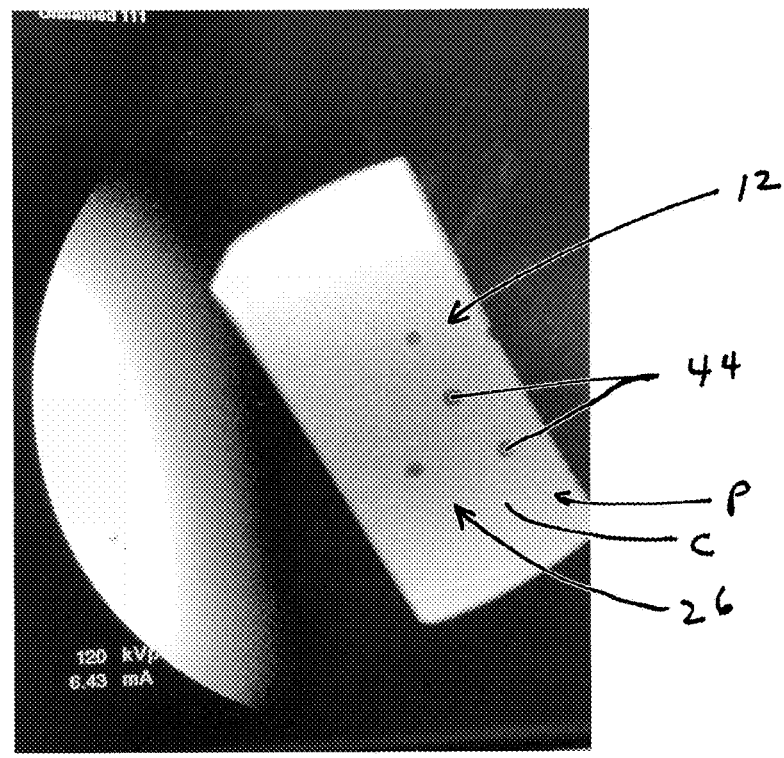
Figure 6:
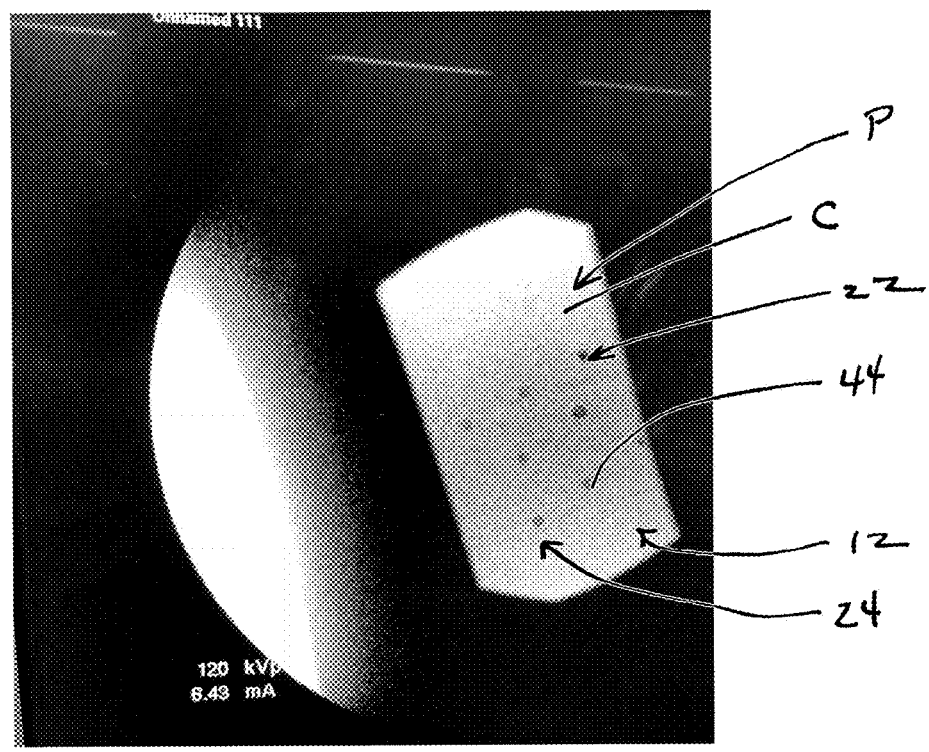

To illustrate the improved visibility of the unique sizes, shapes and patterns of contrast agent in the improved surgical sponge 12, a variety of experimental testing was performed. The results of the testing is shown in FIGS. 4 to 6, which show X-ray images taken of the improved surgical sponges 12 of FIGS. 1 to 3, as filmed through an X-ray phantom specimen. The phantom specimen P in this case was a plastic cylinder C ranging between 32 cm to 36 cm thick in diameter. The plastic cylinder C was of a polymethyl methacrylate material, or PMMA, which has an electron density comparable to water, and thus, the human body. The use of PMMA phantoms is very typical for testing radiation output in fluoroscopic systems, which is the imaging modality used for the experimental testing illustrated here.

As a general matter with respect to the problem of missed surgical sponges, it is noted for purposes of clarity that fluoroscopy uses a feedback mechanism that will adjust the amount of radiation coming from its x-ray tube based on how much radiation is coming into the detector. What drives the feedback system is the amount of radiation attenuation occurring between the tube and detector. As a patient or a specific anatomy of the patient becomes larger (such as the hand vs. the belly) or more dense, the x-ray tube will need to generate more radiation to generate a quality image. However, with increasing radiation (both photon count and photon energy), the likelihood of anatomical details being "washed out" or fading, increases. This would be comparable to an over-exposed picture of a face where it is difficult to make out the details of the nose and cheeks. Such is the problem with the use of increased radiation to locate conventional X-ray sponges missing within a patient, such as a surgical site in a patient's abdomen.

In the illustrated embodiments of FIGS. 4 to 6, 32 cm to 36 cm phantoms P were used to test the sample sponges 12 from the "washing out" phenomenon. In this case, the thickness of the phantom P drove the fluoroscopic system to its maximum x-ray techniques (120 kVp beam energy and 6.43 mA tube current, seen on the x-ray images). Under maximum radiation output, and through 32 cm to 36 cm of tissue-mimicking phantom material P, the contrast agent or fiducials (in this case, bismuth beads) 42, secured to the sponge surface 38 together with the adhesive 40, were readily visible. These maximum x-ray techniques are similar for all fluoroscopic and conventional radiographic systems.

Those skilled in the art will appreciate that the invention described herein is susceptible to variations and modifications other than those specifically described. All such variations and modifications are to be considered within the scope and spirit of the present invention the nature of which is to be determined from the foregoing description.

We claim:

1. A radiologically detectable surgical sponge, comprising,
   a surgical sponge;
   a bismuth contrast agent adhered to a surface of the surgical sponge wherein the bismuth contrast agent is adhered in a unique pattern of spaced dots arranged in rows and columns, and the unique pattern includes spaced dots having different diameters.

2. The radiologically detectable surgical sponge of claim 1, wherein the surgical sponge is a woven surgical sponge material.

3. The radiologically detectable surgical sponge of claim 1, wherein the surgical sponge is a non-woven surgical sponge material.

4. The radiologically detectable surgical sponge of claim 1, wherein the contrast agent and adhesive are applied to the surgical sponge material in a layer having a thickness of between 1 to 2 mm.

5. A radiologically detectable surgical sponge, comprising,
- a woven surgical sponge material;
- a contrast agent, wherein the contrast agent is bismuth beads of between 1 and 5 mm diameter, and an adhesive material adhered to one surface of the surgical sponge material; and
- the contrast agent and adhesive material are adhered to the sponge material in a unique pattern of spaced dots arranged in rows and columns.

6. The radiologically detectable surgical sponge of claim 5, wherein the spaced dots have different diameters.

7. A radiologically detectable surgical sponge, comprising,
- a non-woven surgical sponge material;
- a contrast agent and an adhesive material together adhered to one surface of the surgical sponge material; and
- the contrast agent and adhesive material are adhered to the sponge material in a unique pattern of spaced dots arranged in rows and columns and having different diameters.

8. The radiologically detectable surgical sponge of claim 5, wherein the contrast agent and adhesive are applied to the surgical sponge material in a layer having a thickness of between 1 to 2 mm.

9. The radiologically detectable surgical sponge of claim 5 or 7, wherein the contrast agent and adhesive are applied to the surgical sponge material in a layer having a thickness of between 1.5 to 2 mm.

10. The radiologically detectable surgical sponge of claim 7, wherein the contrast agent is bismuth beads of between 1 and 5 mm diameter.

11. The radiologically detectable surgical sponge of claim 7, wherein the contrast agent is barium sulfate.

12. The radiologically detectable surgical sponge of claim 7, wherein the contrast agent and adhesive are applied to the surgical sponge material in a layer having a thickness of between 1 to 2 mm.

13. A radiologically detectable surgical sponge, comprising,
- a surgical sponge;
- a contrast agent adhered to a surface of the surgical sponge wherein the contrast agent is adhered in a unique pattern of spaced dots arranged in rows and columns, and the unique pattern includes spaced dots having various sizes and spacing.

14. The radiologically detectable surgical sponge of claim 13, wherein the contrast agent is a contrast agent containing barium sulfate.

15. The radiologically detectable surgical sponge of claim 13, wherein the contrast agent is a contrast agent containing bismuth.

* * * * *